United States Patent [19]
Hershline

[11] Patent Number: 5,646,724
[45] Date of Patent: Jul. 8, 1997

[54] THREADED PARTS INSPECTION DEVICE

[75] Inventor: Bruce A. Hershline, Shelby Township, Mich.

[73] Assignee: Candid Logic, Inc., Madison Heights, Mich.

[21] Appl. No.: 521,086

[22] Filed: Aug. 18, 1995

[51] Int. Cl.⁶ ................................................. G01N 21/00
[52] U.S. Cl. ................ 356/237; 250/223 R; 356/398;
33/199 R; 348/86; 348/125; 348/211
[58] Field of Search ....................... 358/101, 106,
358/107, 210, 903; 250/223; 356/237, 398;
33/199

[56] References Cited

U.S. PATENT DOCUMENTS

| | | | |
|---|---|---|---|
| 4,171,161 | 10/1979 | Jung | 356/383 |
| 4,644,394 | 2/1987 | Reeves | 358/101 |
| 4,802,323 | 2/1989 | Garris et al. | 53/53 |
| 4,807,995 | 2/1989 | Dassler et al. | 356/240 |
| 4,906,098 | 3/1990 | Thomas et al. | 356/376 |
| 5,139,150 | 8/1992 | Fuller, Jr. et al. | 209/576 |
| 5,164,995 | 11/1992 | Brooks et al. | 382/8 |

*Primary Examiner*—Frank Gonzalez
*Assistant Examiner*—Michael P. Stafira
*Attorney, Agent, or Firm*—Gifford, Krass, Groh, Sprinkle, Patmore, Anderson & Citkowski, P.C.

[57] ABSTRACT

An opto-electronic, threaded parts inspection device. The device includes a source for generating a thin, planar beam of collimated light which is disposed on one side of a parts carrier. The laser light beam is rotatable about two axes, normal to one another and both normal to the longitudinal axis of parts passing through the beam. A sensor unit is disposed on the other side of the parts carrier so that the light beam falls thereupon. The threaded parts inspection device can be adjusted to pass light over different features of the threaded parts as they are moved past the inspection device by the parts carrier. By measuring how much of the light is interrupted by the profile of the passing threaded parts, it is possible to detect deviations in the pitch angle and major and minor diameters of the threaded workpieces.

11 Claims, 1 Drawing Sheet

THREADED PARTS INSPECTION DEVICE

FIELD OF THE INVENTION

This invention concerns the field of automated optically based inspection systems, and, more particularly, to such systems for detecting defects in a plurality of threaded parts.

DESCRIPTION OF THE RELEVANT PRIOR ART

Concomitant with the rise and spread of automated production systems has been a corresponding rise in the spread of automated inspection systems for detecting faults in the products of automated production systems. While such automated inspection systems are based on a wide variety of physical phenomena (such as ultrasonic waves, x-rays, infrared radiation, etc.), a significant number of such systems are opto-electronic in nature, and rely on one or more beams of electromagnetic radiation as the measuring tool.

In one type of opto-electronic inspection systems, a plurality of nominally identical workpieces are moved on a parts carrier through one or more beams of electromagnetic radiation, such as diffused or coherent light. One or more detectors are provided for detecting the quantity and/or pattern of light passing, defracted, reflected, or scattered by the workpieces. The detectors, which are also opto-electronic, produce signals indicative of the measured light. These signals are then fed to a computational apparatus such as a microprocessor for subsequent processing, often involving comparisons with standard, stored values. Workpieces which deviate from the standard by an unacceptable margin may then be rejected.

Due to continuing refinement in both the optics and receiver parts of the system, such opto-electronic based inspection systems have become increasingly popular. Such systems can detect flaws in the workpieces which are far too small to be visible to the unaided human eye. Thus, such systems are particularly useful in situations where precision is required with high throughput and tolerances in the workpieces are necessarily very small. Thus, opto-electronic based inspection systems lend themselves to the increasingly sophisticated applications engendered by advancing technology.

A number of prior art opto-electronic based inspection systems are disclosed in, for example, U.S. Pat. Nos. 4,802,323; 4,807,995; 4,906,098; 5,139,150; and 5,164,995. In particular, U.S. Pat. No. 5,164,995 discloses a method and apparatus for developing a digital signal that represents the profile of a movable part such as a bolt. The part is moved by a part carrier between a source of radiant energy (such as infrared radiation) and a sensor. As the part passes in front of the source of radiant energy, an electrical signature signal that has a varying voltage over time is developed which indicates the shape and/or orientation of the part. For example, a bolt passing the sensor "head first" would generate a different electrical signature signal than the same bolt passing the sensor "head last." While the system disclosed in this reference appears to function to determine the orientation of a part such as a bolt, there is no indication in the reference that the system can be used to check other attributes of the bolt, such as thread profile, minor diameter, pitch, etc.

In addition, U.S. Pat. No. 4,802,323 discloses an inspection apparatus for inspecting seals of medicinal capsules. Incandescent light is focused through a lens onto a capsule. Light is reflected off the object and onto a photoelectric sensor. A change in the color of the reflected light indicates a defective capsule seal. The inspection apparatus detects the color change in reflected light and produces an electrical signal indicating a defective seal. While the system disclosed in this reference appears to detect defects, it is unable to detect defects due to incorrectly shaped or formed parts.

Common defects in bolts and other threaded parts such as variations in the pitch angle of the thread and variations in the minor and major diameters of the fastener are caused by improper functioning of automated thread cutting equipment. For example, one common defect is called "spiraling" which is a deviation in the pitch of the thread (i.e., the angle the thread makes with an axis normal to the longitudinal axis of the threaded part). Obviously, such defects as spiraling in threaded parts are highly undesirable.

Clearly, it would be desirable to have a system designed to inspect a plurality of threaded workpieces in an automated production environment which is capable of detecting defects in the workpieces not detectable by other systems.

It would be highly desirable to have such an inspection system which is simple in design, and capable of rapidly and repetitively inspecting a plurality of threaded workpieces moving along a conveyor or other type of parts carrier.

SUMMARY OF THE INVENTION

The present invention has been designed to overcome the shortcomings in the prior art noted above. The invention is a system for, and method of, inspecting a plurality of threaded fasteners, each having a longitudinal axis. The threaded fasteners are carried along a path by a parts carrier, such as a conveyor belt or turntable. The system includes a source of collimated light, which may be a laser light, disposed on one side of the parts carrier and which produces a light beam defining a thin plane. The threaded fasteners pass through the light beam as they are conveyed along the path by the parts carrier. The system also includes a sensor disposed on a second, opposing side of the parts carrier that is aligned to detect the light beam generated by the light source. The sensor can be an analog sensor which would generate a voltage proportional to the amount of light passing the workpiece or a linear array of digital sensors. The sensor generates a series of signals over time which indicate the amount of light detected as the threaded fastener passes through the light beam.

The system further includes a computational device, such as a microprocessor, for receiving the signals from the sensor and comparing these signals to preset parameters. In addition, the microprocessor may have a memory for storing the signals received or the results of the comparison of the signals received by the microprocessor from the sensor and the preset parameters. Further, the microprocessor may selectively transmit to another device the results of the comparison.

The light source is preferably supported so as to be rotatable about a first axis which extends normally to the longitudinal axis of the threaded fasteners. This permits the light beam to be adjusted so that adjacent peaks and valleys along one side of a threaded fastener pass through the light beam. If the dimensions of the peaks and valleys are within preset parameters, and the projection of the beam on the fastener is properly adjusted, the amount of the light beam that is blocked by the adjacent peaks and valleys as they are conveyed along the path will remain relatively constant because as the peak of a thread gradually tapers to a valley, the adjacent valley is tapering to a peak. Under these conditions, the sensor should detect a constant amount of light passing by the fastener.

The light source may also be rotated about a second axis which extends normally to both the longitudinal axis of the threaded fastener and the first axis. This permits the light source to be aligned such that the light beam simultaneously strikes a peak of a thread on one side of the fastener and a valley on the opposite side of the threaded fastener. As the threaded fastener passes through a light beam aligned in this manner, the amount of light blocked by the opposing peaks and valleys remains constant if the pitch of the threaded fastener is within preset parameters because the transitions from valley to peak and peak to valley should offset each other.

In the preferred embodiment of the invention, the light source and sensor are supported on a yoke. The yoke is rotatable about the first and second axes, and the light source and sensor mounted on the yoke are rotatable about the first axis, enabling the light beam to be adjusted into either configuration.

BRIEF DESCRIPTION OF THE DRAWING

The following detailed description is best understood by reference to the following drawings, in which.

DETAILED DESCRIPTION OF THE PREFERRED EMBODIMENT

Figure 1:
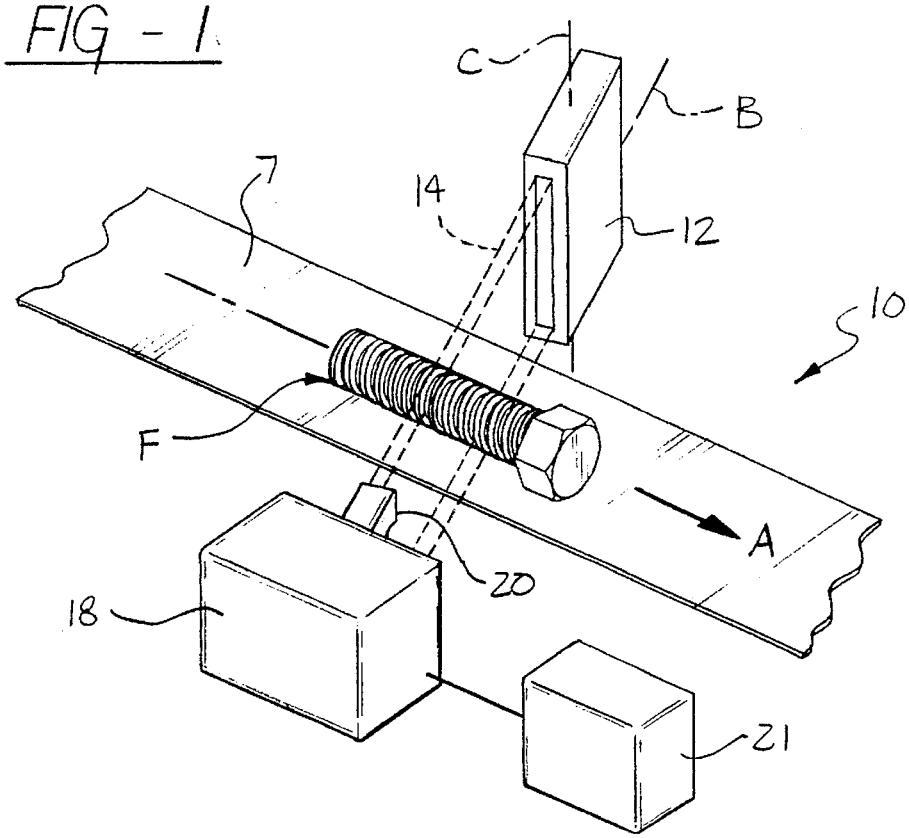
FIG. 1 is a perspective view of an inspection system according to the present invention with some parts thereof shown schematically.

Throughout the following detailed description, like numerals are used to reference the same elements of the invention shown in multiple figures thereof. Referring now to the drawings, and in particular to FIG. 1, there is shown a system 10 for inspecting a plurality of threaded workpieces, such as fastener F, which pass along on a parts carrier, such as conveyor belt 7 shown schematically in FIG. 1. Alternatively, instead of being a linear conveyor belt, the parts carrier could be a rotating turn table, etc.

The system 10 includes a source of collimated light 12 which is disposed on one side of the parts carrier 7 and which produces a light beam 14 defining a thin plane. A plurality of workpieces such as fastener F pass by the light source 12 with their respective longitudinal axis A oriented roughly perpendicular to the light source 12. Thus, the workpieces such as fastener F successively pass through the thin, planar light beam 14. Such light sources, including laser light sources, are well known in the prior art. Typically, a light beam is emitted from a laser diode and converged into a parallel beam by a projecting lens unit. The laser beam is then directed through a slit in the receiver and focused on a light receiving sensor. As workpieces move through the planar beam, changes in the size of the shadow falling on the sensor are translated into a change in received light quantity (such as voltage). The voltage output is typically translated into an analog output for subsequent monitoring. Such laser transmitters and sensors are commercially available through such sources as the Keyence Company.

Figure 2:
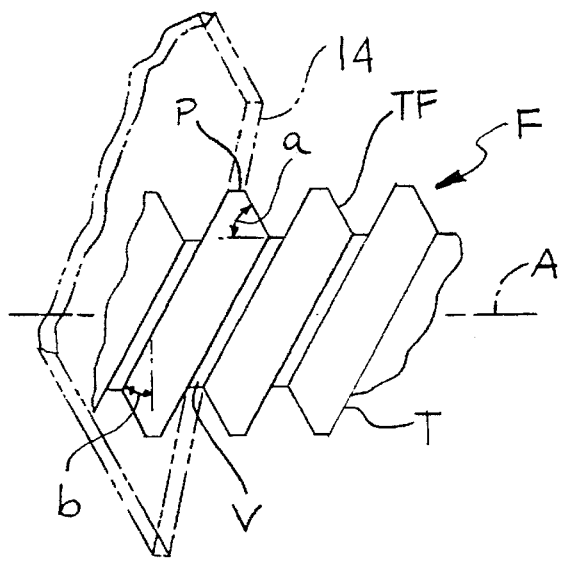
FIG. 2 is a partial, enlarged view of a threaded workpiece passing through a planar light beam generated by the system of the present invention.
Figure 3:
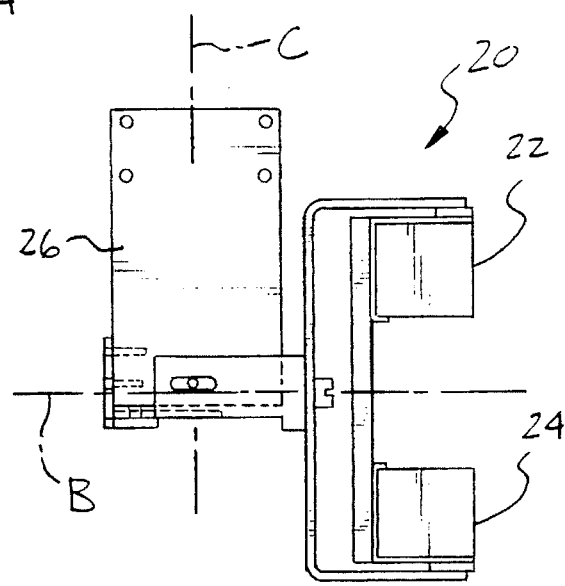
FIG. 3 is a side view of a yoke suitable for use in the system of the present invention.

In the system 10 of the present invention, the light beam 14 produced by the light source 12 is rotatable about a second axis B which extends normally to the longitudinal axis A of the fastener F passing through the beam 14, as well as generally parallel to the plane of the parts carrier 7. As can best be seen in FIG. 2, which is a partial view of a fastener F passing through beam 14, rotation about the axis B will cause the beam 14 to fall simultaneously on a diametrically opposed peak P and valley V of the thread T of fastener F. The exact angle that beam 14 must be rotated about axis B to achieve this will vary, of course, depending on the pitch angle b of the particular fastener. A thread with a smaller pitch angle b will require more rotation of beam 14 about axis B to align the beam with a peak on one side and a valley on the other side of the fastener than a thread with a larger pitch angle b, due to the greater tendency of peaks to align with opposing peaks rather than valleys for smaller pitch angles.

Of course, the pitch angle of the thread should remain constant for any particular series of workpieces, and, in an automated production system, this ideal pitch angle will be predetermined. Beam 14 may be rotated about axis B to correspond to the expected pitch angle. The "shadow" cast by the thread of a part passing through the correctly adjusted beam will remain constant because, as the thread on one side of the workpiece changes from a peak to a valley, it will simultaneously and symmetrically change from a valley to a peak on the other side of the workpiece. Thus, the total amount of the beam blocked by the thread profile must necessarily remain constant as long as the pitch angle remains constant. Thus, any deviations in the amount of passed light will indicate undesirable defects in the pitch of the threaded workpiece.

A receiver 18 is disposed on the second, opposite side of the parts carrier 7. The receiver 18 includes a sensor unit 20 which is disposed in the path of the planar light beam 14. Thus, the succession of workpieces such as fastener F will pass between the light source 12 and the sensor unit 20 and through the planar light beam 14.

The receiver 18 will generate a first electronic signal, such as an analog, voltage-based output, which can be directly observed by a user. Typically, however, the signal will be transmitted to a processing unit 21. Any deviations in the signal transmitted by the receiver 18 can then be compared with standard, preset tolerance values. If, for example, the automated production system is designed to produce workpieces having a certain tolerance, the tolerance values can be loaded into the processing unit 21. Then, if the signal received from the transmitter deviates from the value indicating an ideal pitch angle by more than the preset amount, the processor 21 can generate a defect signal indicating that the particular part is defective. This signal may then be fed to, for example, a parts diverter to deflect the defective part out of the stream of workpieces.

A system 10 of the present invention may also be used to detect deviations in the major and minor diameters of the threaded workpiece. To this end, the beam 14 is rotatable about a third axis C which is perpendicular to both the first and second axis A,B. By rotating the beam 14 about the axis C, the beam may be aligned with the passing thread faces TF of the fastener F. If the beam 14 is rotated to be roughly parallel to axis A, a maximum amount of light will be deflected by the thread faces and the "shadow" cast by the fastener F onto the sensor 20 will be roughly circular. Any deviation in the major diameter, will cause the amount of light passing the fastener F to change.

Defects in the minor diameter of a threaded workpiece can be detected by passing light beam 14 over fastener F such that adjacent peaks and valleys along one side of fastener F deflect a portion of light beam 14. The amount of light passing the fastener F will be determined by the dimensions of the minor diameter and the height of the peaks. As fastener F passes the beam 14, peaks will alternately and symmetrically enter and leave the plane of beam 14. Any deviations in the light received by the sensor 20 will be due to variations in the minor diameter.

Thus, the sensor unit 20 of the present invention is rotatable about both the B and C axes so that the inspection system 10 of the present invention may be used to detect various kinds of thread defects (irregularities in the pitch, major diameter or minor diameter).

In the depicted embodiment 10 of the present invention, a single light beam rotatable about two perpendicular axis has been illustrated, as well as a sensor which is similarly rotatable about both axes. However, the present invention could be advantageously practiced by employing a plurality of separate light beams and sensors, each one of which is rotatable about either the B or C axis, each of which is directed at its companion sensor. One or more non-rotatable light beam and sensor pairs which are oriented at preselected angles could also be employed.

Thus, an apparatus for and method of electronically detecting deviations in pitch and minor and major diameters in a plurality of threaded workpieces has been disclosed with reference to certain depicted exemplifications and embodiments thereof. Doubtless, one of skill in the field of optoelectronic inspection systems, having had the benefit of the teachings of the present invention, could design certain variations in the present system and method without departing from the scope of the invention. Thus, it is the claims appended hereto, and all reasonable equivalents thereof, rather than the exact depicted embodiments and exemplifications, which define the scope of the present invention.

I claim:

1. A device for inspecting an elongated threaded fastener, said fastener having a longitudinal axis defined as being central to the fastener and parallel to its length, the inspection of said fastener taking place as it is moved along a path by a carrier means, said device comprising:

a sensor disposed on a first side of said path, said sensor being rotatable about a first axis extending normally to said longitudinal axis;

a source of collimated light disposed on a second, opposing side of said path for producing a light beam defining a thin plane, said light source being rotatable about said first axis to align said light beam with selected features of said threaded fastener a such that a constant quantity of light is cast on to said sensor as said carrier means moves said threaded fastener along said path;

said sensor generating a signal indicative of said constant quantity of light; and computational means for receiving said signal and determining, on the basis of departures from said constant quantity of light as indicated by said signal, unacceptable deviations in said selected features of said threaded fastener.

2. The device as in claim 1, wherein said light beam is directed at adjacent peaks and valleys along an edge of said threaded fastener.

3. The device as in claim 1, wherein said light beam is directed substantially along a line defining an acute angle with respect to said longitudinal axis of said threaded fastener.

4. The device as in claim 1, where said light source is also rotatable about a second axis extending normally to both said first and said longitudinal axis.

5. The device as in claim 4, wherein said light beam has a height sufficiently large that it may be simultaneously aligned with diametrically opposed peaks and valleys of said threaded fastener.

6. A device for inspecting an elongated threaded fastener, said fastener having a longitudinal axis defined as being central to the fastener and parallel to its length, the inspection of said fastener taking place as it is moved along a path by a carrier means, said device comprising:

a yoke, having a first and second end, and said yoke being rotatable about a first and second axis, said first axis extending normally to said longitudinal axis of said threaded fastener, and said second axis extending normally to both said longitudinal axis and said first axis;

said path and said threaded fastener being interposed between said first and second ends of said yoke;

said first end having a source of collimated light for producing a light beam defining a thin plane;

said second end having a sensor for measuring a quantity of light passing by said threaded fastener and generating a signal indicative of said quantity; and computational means for receiving said signals and determining, on the basis of said signals, unacceptable deviations in selected characteristics of said threaded fastener.

7. A device as in claim 6, wherein said light source is rotatably mounted to said yoke.

8. A device as in claim 6, wherein said light source and sensor are both rotatably mounted to said yoke.

9. A method for inspecting an elongated threaded fastener, said fastener having a longitudinal axis defined as being central to the fastener and parallel to its length, the inspection of said fastener taking place as it is moved along a path, said method comprising:

directing a beam of collimated light past selected features of said fastener such that a constant quantity of light passes said threaded fastener if said features of said threaded fastener are within preset parameters;

sensing the quantity of light passing by said threaded fastener;

generating a signal indicative of said quantity of light received;

transmitting said signal to a computational device;

comparing said signal to said preset parameters; and determining, on the basis of a change between said preset parameters and said signal, whether said features of said threaded fastener deviate unacceptably from said preset parameters.

10. The method of claim 9, wherein the step of directing a beam of collimated light includes the step of directing said beam at adjacent peaks and valleys along an edge of said threaded fastener.

11. The method of claim 9, wherein the step of directing a beam of collimated light includes the step of directing said beam at diametrically opposed peaks and valleys of said threaded fastener.

* * * * *